(12) United States Patent
Knoesche et al.

(10) Patent No.: US 8,765,996 B2
(45) Date of Patent: Jul. 1, 2014

(54) PROCESS FOR PREPARING ISOCYANATES

(75) Inventors: Carsten Knoesche, Niederkirchen (DE); Torsten Mattke, Freinsheim (DE)

(73) Assignee: BASF SE, Ludwigshafen (DE)

( * ) Notice: Subject to any disclaimer, the term of this patent is extended or adjusted under 35 U.S.C. 154(b) by 499 days.

(21) Appl. No.: 13/001,681

(22) PCT Filed: Jul. 23, 2009

(86) PCT No.: PCT/EP2009/059460
§ 371 (c)(1),
(2), (4) Date: Dec. 28, 2010

(87) PCT Pub. No.: WO2010/010135
PCT Pub. Date: Jan. 28, 2010

(65) Prior Publication Data
US 2011/0105785 A1 May 5, 2011

(30) Foreign Application Priority Data
Jul. 23, 2008 (EP) .................................. 08160990

(51) Int. Cl.
C07C 263/10 (2006.01)
C07C 265/14 (2006.01)

(52) U.S. Cl.
CPC ............ C07C 263/10 (2013.01); C07C 265/14 (2013.01)
USPC ....................................................... 560/347

(58) Field of Classification Search
USPC .......................................... 560/347
See application file for complete search history.

(56) References Cited

U.S. PATENT DOCUMENTS

| | | | |
|---|---|---|---|
| 3,507,626 A | 4/1970 | Van Horn | |
| 3,969,449 A * | 7/1976 | Shires et al. | 261/153 |
| 6,803,482 B2 * | 10/2004 | Jenne et al. | 560/347 |
| 6,833,469 B2 * | 12/2004 | Wolfert et al. | 560/347 |
| 6,930,199 B2 * | 8/2005 | Meyn et al. | 560/347 |
| 8,173,833 B2 * | 5/2012 | Woelfert et al. | 560/347 |
| 2003/0069441 A1 | 4/2003 | Leimkuhler et al. | |
| 2004/0192959 A1 | 9/2004 | Woelfert et al. | |
| 2005/0137417 A1 | 6/2005 | Meyn et al. | |

(Continued)

FOREIGN PATENT DOCUMENTS

| | | |
|---|---|---|
| DE | 38 42 065 | 6/1990 |
| EP | 0 289 840 | 11/1988 |

(Continued)

OTHER PUBLICATIONS

International Search Report issued Jan. 4, 2010 in PCT/EP09/059460 filed Jul. 23, 2009.

Primary Examiner — Rosalynd Keys
(74) Attorney, Agent, or Firm — Oblon, Spivak, McClelland, Maier & Neustadt, L.L.P.

(57) ABSTRACT

The invention relates to a process for preparing isocyanates by reacting the corresponding amines with phosgene in the gas phase, if appropriate in the presence of at least one inert medium, the phosgene being passed into a reactor (21) through a first inlet and the amine through a second inlet of an ejector (1). The first inlet and the second inlet open into a mixing zone (17) in which the phosgene and the amine are mixed to give a reaction mixture. The mixing zone (17) is followed downstream by a diffuser (19) in which pressure and temperature of the reaction mixture composed of phosgene and amine are increased.

15 Claims, 1 Drawing Sheet

(56) References Cited

U.S. PATENT DOCUMENTS

| | | |
|---|---|---|
| 2010/0041914 A1 | 2/2010 | Woelfert et al. |
| 2010/0041915 A1 | 2/2010 | Woelfert et al. |
| 2010/0048942 A1 | 2/2010 | Knoesche et al. |
| 2010/0056822 A1 | 3/2010 | Daiss et al. |
| 2010/0076218 A1 | 3/2010 | Daiss et al. |
| 2010/0210870 A1 | 8/2010 | Olbert et al. |
| 2010/0217035 A1 | 8/2010 | Knoesche et al. |
| 2010/0305356 A1 | 12/2010 | Olbert et al. |

FOREIGN PATENT DOCUMENTS

| | | |
|---|---|---|
| EP | 0 928 785 | 7/1999 |
| EP | 1 319 655 | 6/2003 |
| EP | 1 526 129 | 4/2005 |
| EP | 1 555 258 | 7/2005 |
| JP | 2003-96043 A | 4/2003 |
| WO | 2007 028715 | 3/2007 |

* cited by examiner

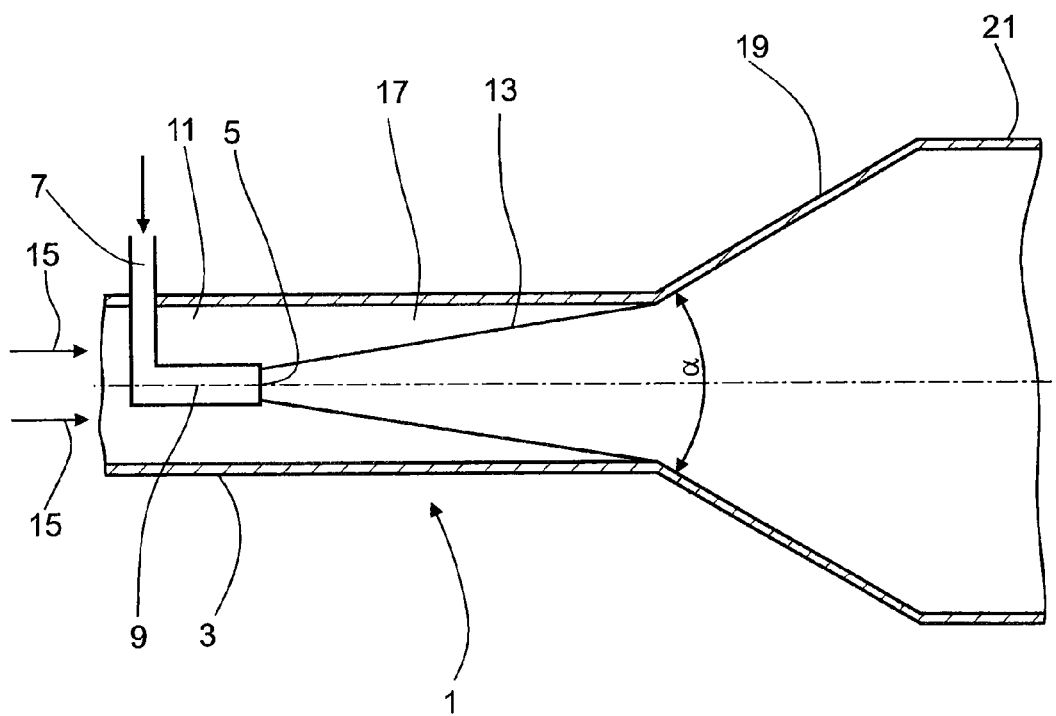

PROCESS FOR PREPARING ISOCYANATES

CROSS REFERENCE TO RELATED APPLICATION

This application is a 371 of PCT/EP2009/059460, filed on Jul. 23, 2009, and claims priority to European Patent Application No. 08160990.1, filed on Jul. 23, 2008.

The invention relates to a process for preparing isocyanates by reacting the corresponding amines with phosgene in the gas phase, if appropriate in the presence of at least one inert medium, the phosgene being passed into a reactor through a first inlet and the amine through a second inlet of an ejector.

Isocyanates can in principle be prepared by phosgenating the corresponding amines by a liquid phase phosgenation or a gas phase phosgenation. In gas phase phosgenation, a higher selectivity, a lower holdup of toxic phosgene and a reduced amount of energy are required.

In gas phase phosgenation, an amine-containing reactant stream and a phosgene-containing reactant stream are mixed each in the gaseous state. The amine and the phosgene are reacted with release of HCl to give the corresponding isocyanates. The amine-containing reactant stream is generally present in the liquid phase and has to be evaporated and if appropriate superheated before being mixed with the phosgene-containing stream.

Owing to the low vapor pressure, especially of the diamines, the evaporation is effected at elevated temperature. However, this also causes decomposition reactions of the amines or diamines, for example deaminations, demethylations, dimerizations, which have an adverse effect on the selectivity of the overall process.

In addition, when the two reactant streams are contacted, reactive conversions rapidly set in owing to the high temperatures. In addition to the phosgenation of the amine to the isocyanate, undesired side reactions and subsequent reactions can set in. For example, isocyanate which has already formed can form a urea with amine which has yet to be depleted. In addition, carbodiimides and cyanurates can also form. This firstly has an adverse effect on the selectivity of the process, and solid by-products formed can secondly lead to blockages and thus have an adverse effect on the run time of the plant. Therefore, it is generally attempted to mix the reactant streams very rapidly in order to as far as possible avoid mixing conditions which accelerate the formation of secondary components.

For example, EP-A 1 319 655 discloses preparing diisocyanates and triisocyanates by heating the corresponding vaporous di- and/or triamines and phosgene separately to temperatures in the range from 200° C. to 600° C. and passing them through a static mixing unit, wherein the gaseous reactants flow through a reactor in parallel and the amine is fed to the reactor through a nozzle in the mixing unit and the phosgene through an annular space surrounding the nozzle. The annular space has the same diameter as the reactor. The velocity of the amine is high compared to the velocity of the phosgene.

EP-A 0 928 785 discloses mixing amine and phosgene in a microstructured mixer. In this case, the reactants emerge from the component in the form of thin free jets, where they then mix very rapidly as a result of diffusion and/or turbulence. This accelerates the mixing operation and increases the achievable yield.

The preparation of isocyanates by phosgenation of the corresponding amines in a tubular reactor which has an elongated, jacketed guide tube centrally in the direction of the axis of rotation of the tubular reactor is described in EP-A 1 555 258. Between the inner and outer walls of the jacketed guide tube, a concentric annular gap is formed. For the reaction, vaporous diamines and/or triamines and phosgene are heated separately from one another to temperatures in the range from 200° C. to 600° C. and then the vaporous diamines and/or triamines are fed to the tubular reactor via the concentric annular gap, and the phosgene over the remaining cross-sectional area of the tubular reactor.

EP-A 1 526 129 describes a process for preparing isocyanate, in which a reactant stream comprising diamines and/or triamines is supplied to a tubular reactor via an annular space which surrounds a central nozzle, and a phosgene-comprising reactant stream is supplied via the central nozzle. The annular space has the same diameter as the reactor. To generate turbulence, a turbulence generator is arranged in the central nozzle.

EP-A 0 289 840 also discloses first introducing phosgene through a nozzle which projects into a mixing tube. An amine is introduced through an annular gap which surrounds the nozzle. Before being introduced, the phosgene and the amine are heated to a temperature in the range from 200 to 600° C., preferably from 200 to 500° C.

A disadvantage of all known processes is that, owing to the high temperatures, the reaction sets in immediately with the mixing and, owing to the simultaneous presence of amine and isocyanate, corresponding ureas are also formed in a side reaction.

DE-A 38 42 065 discloses evaporating a high-boiling substance by using an ejector. A first reactant is passed with a high velocity through the ejector within a central nozzle. This pulls in the second reactant from an annular space. This gives rise to a reduced pressure in the region of the feed of the second reactant to the reactor. For this reason, it is possible to evaporate at a lower temperature. However, this leads to the effect that reaction mixture leaving the ejector has a temperature which is below the suitable reaction temperature.

It is an object of the present invention to provide a process for preparing isocyanates by reacting the corresponding amines with phosgene in the gas phase, which enables rapid mixing of the reactants and a further reduction in the formation of by-products.

The object is achieved by a process for preparing isocyanates by reacting the corresponding amines with phosgene in the gas phase, if appropriate in the presence of at least one inert medium, the phosgene being passed into a reactor through a first inlet and the amine through a second inlet of an ejector. The first inlet and the second inlet open into a mixing zone in which the phosgene and the amine are mixed to give a reaction mixture. The mixing zone is followed downstream by a diffuser in which pressure and temperature of the reaction mixture composed of phosgene and amine are increased.

The phosgene preferably enters the mixing zone at least sonic velocity. This results in a velocity typically of more than 0.5 Ma in the mixing zone, and so the temperature in the mixing zone is significantly lower than in the reactor. In addition, the pressure in the mixing zone is also lower than in the reactor. Evaporation of the amine at lower temperatures is achieved by significantly reducing the pressure in the feed line of the amine to the mixing zone relative to the pressure in the reactor.

The first inlet and the second inlet, which open into the mixing zone, are preferably a central nozzle and an annular gap surrounding the central nozzle. In a preferred embodiment, the phosgene is passed through the central nozzle and the amine through the annular gap surrounding the central nozzle. However, it is alternatively also possible that the phosgene is added through the annular gap surrounding the central nozzle, and the amine through the central nozzle.

When the phosgene is added via the annular gap surrounding the central nozzle, the tendency to form deposits is lower than in the case of addition of the phosgene via the central nozzle. However, the addition of the phosgene via the annular gap surrounding the central nozzle is disadvantageous with regard to the pressure drop. Typically, the phosgene is therefore supplied via the central nozzle.

The ejector achieves rapid mixing of the phosgene with the amine. Owing to the high velocity of the phosgene, the flow through the mixing zone downstream of the nozzle is turbulent, thus giving rise to mixing owing to turbulence. In the diffuser downstream of the mixing zone, the temperature and the pressure are increased relative to the mixing zone. This enables the mixing of phosgene and amine in the mixing zone to be performed at a temperature which is below the temperature at which the reaction proceeds at maximum reaction rate. At the same time, the partial pressures of phosgene and amine are also reduced. This results in a lower reaction rate in the mixing zone. Owing to the lower reaction rate in the mixing zone, less isocyanate is prepared. As a result, it is possible to reduce the formation of by-products, especially of urea, resulting from the simultaneous presence of isocyanate and amine. The temperature rise to the actual reaction temperature and the reaction pressure proceeds in the diffuser.

Owing to the rapid flow of the phosgene, preferably through the central nozzle, a reduced pressure is generated in the amine supply, i.e., in the case of phosgene added via the central nozzle, in the annular gap surrounding the central nozzle and the feed opening into the annular gap. Since the boiling point of a substance depends on the pressure and the boiling point also falls at lower pressure, the amine is thus evaporated at lower temperatures with decreasing pressure. The evaporation at lower temperatures allows the amine to be evaporated more gently.

The pressure which can be achieved in the amine supply and hence in the feed of the amine depends on the velocity of the phosgene and the geometric dimensions of nozzle and annular gap. The pressure in the annular gap and the feed decreases with increasing velocity of the phosgene.

Suitable pressures which are achieved in the amine supply and in the feed of the amine, preferably in the annular gap and in the feed opening into the annular gap, generally depend on the amine used. The pressure in the feed of the amine is preferably in the range from 0.01 to 3 bara, especially in the range from 0.05 to 1.5 bara.

The pressure in the mixing zone is preferably within a range from 0.05 to 3 bara and the temperature in the mixing zone within a range from 200 to 400° C. The pressure and the temperature in the mixing zone arise from the pressure and the temperature of the phosgene and amine flowing into the mixing zone. The phosgene flowing into the mixing zone is preferably heated to a temperature in the range from 250 to 450° C.

To heat the phosgene and the amine and to simultaneously evaporate the amine, for example, an electrical heater or direct or indirect heating by combustion of a fuel are used. The fuels used are typically fuel gases, especially natural gas. As a result of the lowering of the boiling point of the amine, however, heating, for example by steam, is also possible. The pressure of the steam here is selected according to the boiling point of the amine. A suitable vapor pressure of the steam is, for example, in the range from 40 to 100 bar. This gives rise to a temperature of the steam in the range from 250 to 311° C.

In general, it is necessary to heat the amine to the reaction temperature in several stages. In general, for this purpose, the amine is first preheated, then evaporated and then superheated. In general, the evaporation requires the longest residence times and thus leads to decomposition of the amine. In order to minimize this, evaporation at lower temperatures, as arise, for example, as a result of the lower pressure, is advantageous. In order to superheat the evaporated amine to reaction temperature after the evaporation, heating with steam is generally insufficient. For the superheating, an electrical heater or direct or indirect heating by burning a fuel is therefore typically used.

In contrast to the evaporation of the amine, the evaporation of the phosgene is generally effected at significantly lower temperatures. For this reason, steam can generally be used to evaporate the phosgene. However, the necessary superheating of the phosgene to heat it to reaction temperature is generally possible only by electrical heating or direct or indirect heating by burning a fuel.

In the diffuser, the temperature of the reaction mixture is increased to reaction temperature. At the same time, the pressure is also increased to reaction pressure. The pressure and temperature increase arises from the geometric configuration of the diffuser. Depending on the amine used, the temperature in the diffuser is raised preferably to from 250 to 450° C. and the pressure to from 0.5 to 3 bara. More preferably, the temperature to which the reaction mixture is heated in the diffuser is in the range from 300 to 400° C. The pressure to which the reaction mixture is compressed is more preferably in the range from 0.8 to 3.0 bara.

The phosgene is accelerated in the first inlet, preferably in the central nozzle, but alternatively in the annular gap, to sonic velocity or supersonic velocity, for example with the aid of a Laval nozzle. As a result of this, the phosgene emerges from the nozzle with sonic velocity or supersonic velocity. Depending on the pressure conditions in the mixing zone, the phosgene can expand further to higher speeds after exiting from the central nozzle.

The sonic velocity of a gas generally depends on the temperature. The higher the temperature, the greater is the supersonic velocity. Advantageously, the temperature of the phosgene which flows into the mixing zone through the central nozzle is in the range from 250 to 450° C. The sonic velocity of the phosgene at the nozzle exit is thus preferably in the range from 210 to 254 m/s. The entry velocity of the phosgene into the mixing zone corresponds preferably at least to the sonic velocity. A suitable geometric configuration of the phosgene feed, for example in the form of a Laval nozzle, allows acceleration over and above sonic velocity, i.e. to supersonic velocity.

The high velocity in the mixing zone leads to reduced temperatures and a lower pressure. The phosgene is thus mixed with the amine at lower temperatures and pressures and hence at a low reaction rate. This allows side reactions to be reduced in the unmixed state and higher selectivities to be achieved. Only after complete mixing with entry into the diffuser is the reaction rate accelerated by the buildup of pressure and temperature. The high velocities which occur in the mixing zone additionally reduce the deposition tendency of any solids formed, for example ureas, uretdiones, isocyanurates, hydrochlorides or biurets, and so advantages are also obtained in the run time of the plant.

The exit velocity of the phosgene from the central nozzle or alternatively from the annular gap, depending on the geometry of the central nozzle and of the annular gap, preferably gives rise to a velocity with which the amine exits from the annular gap or from the central nozzle in the range from 30 to 160 m/s. The amine more preferably exits from the annular gap or from the central nozzle with a velocity in the range from 50 to 150 m/s.

In order to achieve complete mixing of the phosgene with the amine in the mixing zone, it is preferred when the ratio of length to diameter of the mixing zone (L/D ratio) is greater than 2. At the same time, it is preferred when the L/D ratio is not greater than 10, in order that the pressure and the temperature and hence the reaction rate are increased as a result of entry into the diffuser as fast as possible after the complete mixing of amine and phosgene. The L/D ratio is more preferably in the range from 4 to 7.

Rapid mixing of phosgene and amine in the mixing zone and the desired lowering of temperature and pressure are achieved by virtue of the mean velocity in the mixing zone preferably being in the range from 50 to 260 m/s. The mean velocity in the mixing zone is more preferably in the range from 100 to 250 m/s. This velocity is achieved especially by virtue of the exit velocity of the phosgene from the central nozzle. In the diffuser connected downstream of the mixing zone, the velocity of the reaction mixture is reduced. As a result, pressure and temperature rise. To achieve the temperature required for the phosgenation of the amine, the velocity at the exit of the diffuser is preferably in the range from 1 to 50 m/s. The velocity of the reaction mixture at the exit from the diffuser is more preferably in the range from 2 to 30 m/s.

The diffuser is followed downstream by a customary reactor, as used for the performance of the phosgenation of an amine to prepare isocyanates. Reactors generally used are tubular reactors. The diameter of the tubular reactor corresponds preferably to the exit diameter of the diffuser.

In order to achieve the reduction in the velocity in the diffuser and hence the necessary pressure and temperature buildup, the diffuser preferably has an opening angle in the range from 4 to 20°. The ratio of the length of the diffuser, based on the diameter at the diffuser exit, is preferably in the range from 3 to 14. The diffuser more preferably has an opening angle in the range from 6 to 16°, and the ratio of the length of the diffuser, based on the diameter at the diffuser exit, is in the range from 3.5 to 9.5.

To achieve rapid mixing of phosgene and amine and in order to achieve the necessary pressure drop in the second inlet through which the amine is added, it is preferred when the ratio of the opening cross section of the second inlet to the opening cross section of the first inlet through which the phosgene is added is in the range from 1 to 20. The ratio of the opening cross section of the second inlet to the opening cross section of the first inlet through which the phosgene is added is preferably in the range from 1.2 to 15. The ratio is most preferably in the range from 1.5 to 10.

The ratio of the opening cross section of the annular gap to the opening cross section of the nozzle also gives rise to the ratio of phosgene to amine in the reaction mixture. The proportion of amine depends on the velocity with which the amine is sucked through the annular gap into the mixing zone and also on the cross section of the annular gap. The greater the cross section and the higher the velocity of the amine, the greater is the proportion of amine. In order to supply only the proportion of amine needed for the reaction through the annular gap into the mixing zone, it is possible to mix the amine with an inert gas. In particular, to avoid the formation of by-products, preference is given to supplying phosgene in excess. The proportion of inert gas in the amine allows the amount of amine supplied to be established with a given geometry of central nozzle and annular gap and a given velocity and hence volume flow of the phosgene. Inert media which are added are those which are present in gaseous form in the reaction chamber and do not react with compounds which occur in the course of the reaction. The inert media used may, for example, be nitrogen, noble gases such as helium or argon, aromatics such as chlorobenzene, chlorotoluene, o-dichlorobenzene, toluene, xylene, chloronaphthalene, decahydronaphthalene, carbon dioxide or carbon monoxide. However, preference is given to using nitrogen and/or chlorobenzene as the inert medium.

Alternatively, it is, however, also possible, for example in order to avoid too great an excess of phosgene, to add the phosgene to the inert medium.

In general, the inert medium is added in an amount such that the ratio of the gas volumes of inert medium to amine or to phosgene is from more than 0.0001 to 30, preferably from more than 0.01 to 15 and more preferably from more than 0.1 to 5.

Amines which can be used to prepare isocyanates are monoamines, diamines, triamines or higher-functionality amines. Preference is given to using monoamines or diamines. According to the amine used, the corresponding monoisocyanates, diisocyanates, triisocyanates or higher-functionality isocyanates are formed. Preference is given to preparing monoisocyanates or diisocyanates by the process according to the invention.

The amines and isocyanates may be aliphatic, cycloaliphatic or aromatic. The amines are preferably aliphatic or cycloaliphatic, more preferably aliphatic.

Cycloaliphatic isocyanates are those which comprise at least one cycloaliphatic ring system.

Aliphatic isocyanates are those which have exclusively isocyanate groups which are bonded to straight or branched chains.

Aromatic isocyanates are those which have at least one isocyanate group bonded to at least one aromatic ring system.

In the context of this application, (cyclo)aliphatic isocyanates are an abbreviated representation of cycloaliphatic and/or aliphatic isocyanates.

Examples of aromatic monoisocyanates and diisocyanates are preferably those having from 6 to 20 carbon atoms, for example phenyl isocyanate, monomeric methylene 2,4'- and/or 4,4'-di(phenyl isocyanate) (MDI), tolylene 2,4- and/or 2,6-diisocyanate (TDI) and naphthyl 1,5- or 1,8-diisocyanate (NDI).

Diisocyanates are preferably (cyclo)aliphatic diisocyanates, more preferably (cyclo)aliphatic diisocyanates having from 4 to 20 carbon atoms.

Examples of customary diisocyanates are aliphatic diisocyanates such as tetramethylene 1,4-diisocyanate, hexamethylene diisocyanate (1,6-diisocyanatohexane), octamethylene 1,8-diisocyanate, decamethylene 1,10-diisocyanate, dodecamethylene 1,12-diisocyanate, tetradecamethylene 1,14-diisocyanate, 1,5-diisocyanatopentane, neopentane diisocyanate, derivatives of lysine diisocyanate, tetramethylxylylene diisocyanate (TMXDI), trimethylhexane diisocyanate or tetramethylhexane diisocyanate, and also 3 (or 4), 8 (or 9)-bis(isocyanatomethyl)tricyclo[$5.2.1.0^{2,6}$]decane isomer mixtures, and also cycloaliphatic diisocyanates such as 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)-cyclohexane (isophorone diisocyanate), 1,3- or 1,4-bis(isocyanatomethyl)cyclohexane, 2,4- or 2,6-diisocyanato-1-methylcyclohexane.

Preference is given to 1,6-diisocyanatohexane, 1-isocyanato-3,3,5-trimethyl-5-(isocyanatomethyl)cyclohexane, 4,4'-di(isocyanatocyclohexyl)methane and tolylene diisocyanate isomer mixtures. Particular preference is given to 1,6-diisocyanatohexane, 1-isocyanato-3,3,5-trimethyl-5-(isocyanatomethyl)cyclohexane and 4,4'-di(isocyanatocyclohexyl)methane.

Amines which are used in the process according to the invention for the reaction to give the corresponding isocyanates are those for which the amine, the corresponding intermediates and the corresponding isocyanates are present in gaseous form under the selected reaction conditions. Preference is given to amines which, during the reaction, decompose under the reaction conditions to an extent of at most two mol %, more preferably to an extent of at most 1 mol % and most preferably to an extent of at most 0.5 mol %. Particularly suitable here are amines, especially diamines, based on aliphatic or cycloaliphatic hydrocarbons having from 2 to 18 carbon atoms. Examples thereof are 1,6-diaminohexane, 1,5-diaminopentane, 1,3-bis(aminomethyl)-cyclohexane, 1-amino-3,3,5-trimethyl-5-aminomethylcyclohexane (IPDA) and 4,4'-diaminodicyclohexylmethane. Preference is given to using 1,6-diaminohexane (HDA).

It is likewise possible to use aromatic amines for the process according to the invention, which can be converted to the gas phase without significant decomposition. Examples of preferred aromatic amines are tolylenediamine (TDA), as the 2,4- or 2,6-isomer or as a mixture thereof, for example as an 80:20 to 65:35 (mol/mol) mixture, diaminobenzene, 2,6-xylidine, naphthyldiamine (NDA) and 2,4'- or 4,4'-methylene (diphenylamine) (MDA) or isomer mixtures thereof. Among these, preference is given to the diamines, particular preference to 2,4- and/or 2,6-TDA or 2,4'- and/or 4,4'-MDA.

To prepare monoisocyanates, it is likewise possible to use aliphatic, cycloaliphatic or aromatic amines, typically monoamines. A preferred aromatic monoamine is especially aniline.

In the gas phase phosgenation, the aim is that the compounds which occur in the course of the reaction, i.e. reactants (amine and phosgene), intermediates (especially the mono- and dicarbamoyl chlorides which form as intermediates), end products (diisocyanate), and any inert compounds metered in, remain in the gas phase under the reaction conditions. Should these or other components be deposited out of the gas phase, for example on the reactor wall or other apparatus components, these depositions can undesirably alter the heat transfer or the flow of the components in question. This is especially true of amine hydrochlorides which occur, which form from free amino groups and hydrogen chloride, since the resulting amine hydrochlorides precipitate out readily and are reevaporable only with difficulty.

In addition to the use of a tubular reactor, it is also possible to use essentially cuboidal reaction chambers, for example plate reactors. In this case, the diffuser is configured such that the exit cross section of the diffuser corresponds to the cross section of the reactor. The length of the reactor is preferably selected independently of the cross-sectional shape such that the amine is converted essentially fully to the corresponding isocyanate within the reactor. The contact time of the reaction mixture for this purpose is generally between 0.001 s and less than 5 s, preferably from 0.01 to 3 s, more preferably from 0.015 to less than 2 s. In the case of the conversion of (cyclo) aliphatic amines, the mean contact time may be more preferably 0.015 to 1.5 s, especially from 0.015 to 0.5 s, especially from 0.02 to 0.1 s and often from 0.025 to 0.05 s. The contact time is established through the velocity of the reaction mixture within the reactor and the reactor length.

Mean contact time is understood to mean the time span from the commencement of mixing of the reactants until they leave the reaction chamber in a workup stage. In a preferred embodiment, the flow in the reactor of the process according to the invention is characterized by a Bodenstein number of more than 10, preferably more than 100 and more preferably more than 500.

Owing to the high velocities which still prevail even at the exit of the diffuser, the flow in the reactor is typically turbulent. As a result, narrow residence time distributions with low standard deviation of usually not more than 6 percent and good mixing are achieved. A constriction in the reactor, which is additionally prone to blockage, is not needed. However, it may be advisable to incorporate flow homogenizers, for example, into the reactor, as are known to those skilled in the art.

If necessary, the temperature of the reaction volume can be controlled. Typically, the temperature is controlled through the jacket of the reactor. In order to build production plants with high plant capacity, it is possible to connect a plurality of reactor tubes in parallel. In this case, the feed into each individual reactor tube is via the central nozzle with the surrounding annular space and the downstream mixing zone and diffuser. The individual tubes are typically arranged as a tube bundle in a tube bundler reactor. In addition to temperature control of the reactors, it is, though, also possible to perform the reaction, for example, adiabatically. In this case, the individual reactors are typically thermally insulated.

The reactor is typically followed downstream by a processing unit. In general, the gaseous mixture which leaves the reactor is preferably scrubbed with a solvent at temperatures of more than 130° C. Suitable solvents are preferably hydrocarbons which are optionally substituted by halogen atoms. Suitable solvents are, for example, hexane, benzene, 1,3,5-trimethylbenzene, nitrobenzene, anisole, chlorobenzene, chlorotoluene, o-dichlorobenzene, trichlorobenzene, diethyl isophthalate (DEIP), tetrahydrofuran (THF), dimethylformamide (DMF), xylene, chloronaphthalene, decahydronaphthalene and toluene. The solvent used is more preferably monochlorobenzene. However, the solvent used may also, for example, be the isocyanate. The scrubbing transfers the isocyanate selectively into the wash solution. Subsequently, the remaining gas and the resulting wash solution are preferably separated by means of rectification into isocyanate, solvent, phosgene and hydrogen chloride.

The gas mixture leaving the reactor is scrubbed preferably in a scrubbing tower, in which case the isocyanate formed is removed from the gaseous mixture by condensation in an inert solvent, whereas excess phosgene, hydrogen chloride and if appropriate the inert medium pass through the workup apparatus in gaseous form. Preference is given to keeping the temperature of the inert solvent above the dissolution temperature of the carbamyl chloride corresponding to the amine in the selected scrubbing medium. Particular preference is given to keeping the temperature of the inert solvent above the melting point of the carbamyl chloride corresponding to the amine.

The scrubbing can be carried out in any desired apparatus known to those skilled in the art. Suitable examples are stirred vessels or other conventional apparatus, for example columns or mixer-settler apparatus.

The scrubbing and the workup of the mixture leaving the reactor are effected generally as described, for example, in WO-A 2007/028715.

The invention will be illustrated in detail hereinafter with reference to a drawing.

The sole FIGURE shows a schematic of an ejector for performing the process according to the invention.

An ejector 1 comprises a tube 3 which opens into a central nozzle 5. The tube 3 surrounds a feed 7 to the central nozzle 5. The feed 7 has a tubular configuration and has a section 9 which runs along the axis of the tube 3. In this way, an annular gap 11 is formed between the section 9 of the feed 7 and the tube 3 surrounding the section 9 of the feed 7.

Phosgene is supplied to the ejector 1 via the feed 7. The phosgene emerges from the feed 7 via the central nozzle 5 with a high velocity. The phosgene preferably exits from the central nozzle 5 at sonic velocity.

The phosgene exiting from the central nozzle 5 forms a widening jet 13, which entrains medium from the environment. This gives rise to a reduced pressure in the annular gap 11. The reduced pressure which arises in the annular gap 11 sucks in an amine, for example from a reservoir vessel which comprises the amine, and the amine flows through the annular gap 11 and passes into the mixing zone 17 which is connected downstream of the central nozzle 5 in the tube 3. The inflow of the amine is shown in the FIGURE by arrows 15.

In the mixing zone 17 which follows downstream of the central nozzle 5 in the tube 3, the phosgene flowing out of the central nozzle 5 and the amine entrained from the annular gap 11 by the phosgene mix to give a reaction mixture. Owing to the high velocity of the phosgene, the flow in the mixing zone 17 is turbulent and amine and phosgene are mixed rapidly.

As described above, the amine and/or the phosgene may if appropriate comprise an inert medium. Preference is given to using nitrogen or chlorobenzene as the inert medium.

Owing to the reduced pressure in annular gap 11, the amine evaporates actually at temperatures below the preferred reaction temperature. As a result, the reaction velocity of the amine with the phosgene in the mixing zone 17 is reduced and less isocyanate is formed. The amount of by-products, which can be formed, for example, through reaction of the isocyanate with the amine, likewise decreases at a result.

The mixing zone 17 is followed downstream by a diffuser 19. In the diffuser 19, the flow cross section generally increases constantly. To this end, the diffuser 19 has an opening angle α in the range from 4 to 20°, preferably from 6 to 16°.

In the diffuser 19, the velocity of the reaction mixture decreases. At the same time, the pressure rises and, with the pressure, also the temperature. The length of the diffuser 19 is preferably selected such that the reaction temperature required for a high reaction velocity and the corresponding pressure exist at the diffuser exit.

The diffuser 19 is followed downstream by a reactor 21 in which the amine is reacted with the phosgene to give the isocyanate. The reactor is preferably configured as a tubular reactor.

The reactor may be followed downstream by a processing unit for the product mixture comprising the isocyanate.

EXAMPLE

In an inventive injector nozzle, 1.75 kg/h of toluoylenediamine and 8.5 kg/h of phosgene are mixed. The toluoylenediamine is present in the form of an 80:20 isomer mixture of 2,4- and 2,6-TDA. The reaction is carried out at a starting temperature of 400° C. and a pressure of 2 bara.

The phosgene is supplied via a central nozzle with a diameter of 1.6 mm and opens into a mixing tube with an internal diameter of 2.9 mm and an L/D ratio of 6. The entry cross section for the amine is 4.6 mm². The upstream pressure of the phosgene needed is 4.4 bara. This gives rise to a theoretical velocity in the mixing tube of 190 m/s. The phosgene exits from the nozzle with sonic velocity of 245 m/s. As a result of the acceleration of the phosgene, it cools to 360° C. The pressure which is established at the start of the mixing zone and in the suction line of the amine is thus approx. 1.25 bara. Owing to the lowering of the pressure from 2 bara to 1.25 bara, the boiling point of the amine can be lowered from 315° C. to 295° C. Owing to the reduced partial pressures of the reactants, the reaction rate at the start of the mixing zone is more than 60% lower than under the conditions which exist in the reactor.

In the diffuser which is connected downstream of the mixing zone and has an opening angle of 12°, the diameter widens from 2.9 mm to 18 mm. The temperature of the reaction mixture which flows through the diffuser increases to 400° C., and the pressure to 2 bara.

LIST OF REFERENCE NUMERALS

1 Ejector
3 Tube
5 Central nozzle
7 Feed
9 Section of feed 7
11 Annular gap
13 Widening jet
15 Amine feed
17 Mixing zone
19 Diffuser
21 Reactor
α Opening angle

The invention claimed is:

1. A process for preparing an isocyanate, comprising:
passing a phosgene into a reactor through a first inlet of said reactor;
passing an amine into said reactor through a second inlet of said reactor, thereby introducing said phosgene and said amine into a mixing zone of said reactor to mix said phosgene and said amine; and
reacting said amine with said phosgene in a gas phase, optionally in the presence of at least one inert medium, to obtain an isocyanate,
wherein
the first inlet and the second inlet open into said mixing zone in which the phosgene and the amine are mixed to give a reaction mixture and the mixing zone is followed downstream by a diffuser in which pressure and temperature of the reaction mixture comprising said phosgene and said amine are increased, and
the flow of the phosgene through the first inlet generates a reduced pressure in the second inlet and in a feed of the amine opening into the second inlet.

2. The process according to claim 1, wherein the pressure in the second inlet and in the feed opening into the second inlet is in the range from 0.01 to 3 bara.

3. The process according to claim 1, wherein the first inlet is a central nozzle and the second inlet is an annular gap of the injector surrounding the central nozzle.

4. The process according to claim 1, wherein the pressure in the mixing zone is within a range from 0.05 to 3 bara and the temperature in the mixing zone is within a range from 200 to 400° C.

5. The process according to claim 1, wherein the temperature is increased to from 250 to 450° C. and the pressure to from 0.5 to 3 bara in the diffuser.

6. The process according to claim 3, wherein the velocity with which the phosgene leaves the central nozzle is sonic velocity or supersonic velocity.

7. The process according to claim 3, wherein the velocity with which the phosgene leaves the central nozzle is in the range from 200 to 500 m/s.

8. The process according to claim 3, wherein the velocity with which the amine leaves the annular gap is in the range from 30 to 160 m/s.

9. The process according to claim 1, wherein the ratio of length to diameter of the mixing zone is in the range from 2 to 10.

10. The process according to claim 1, wherein the mean velocity in the mixing zone is in the range from 100 to 250 m/s and the mean velocity of the reaction mixture at the exit from the diffuser is in the range from 1 to 50 m/s.

11. The process according to claim 1, wherein the diffuser has an opening angle in the range from 4 to 20° and the ratio of the length of the diffuser based on the diameter of the diffuser at the diffuser exit is in the range from 3 to 14.

12. The process according to claim 1, wherein the ratio of the opening cross section of the second inlet through which the amine is added to the opening cross section of the first inlet through which the phosgene is added is in the range from 1 to 20.

13. The process according to claim 1, wherein the isocyanate is a monoisocyanate or diisocyanate.

14. The process according to claim 1, wherein the amine is at least one member selected from the group consisting of
1,6-diaminohexane; monomeric 2,4'-methylene(diphenylamine); 4,4'-methylene(diphenylamine); 2,4-toluylenediamine; 2,6-toluylenediamine; and 1-amino-3,3,5-trimethyl-5-aminomethylcyclohexane.

15. The process according to claim 1, wherein the diffuser has an opening angle in the range from 4 to 20°, and said phosgene, upon exiting a central nozzle connected to said first inlet, enters the mixing zone at a widening angle.

* * * * *